(12) United States Patent
Park

(10) Patent No.: US 9,198,799 B2
(45) Date of Patent: Dec. 1, 2015

(54) SKI GOGGLES HAVING PRESSURE BALANCER

(71) Applicant: KOREA O.G.K CO., LTD., Wonju (KR)

(72) Inventor: Soo An Park, Seoul (KR)

(73) Assignee: KOREA O.G.K CO., LTD. (KR)

( * ) Notice: Subject to any disclaimer, the term of this patent is extended or adjusted under 35 U.S.C. 154(b) by 0 days.

(21) Appl. No.: 14/492,188

(22) Filed: Sep. 22, 2014

(65) Prior Publication Data

US 2015/0297410 A1  Oct. 22, 2015

(30) Foreign Application Priority Data

Apr. 20, 2014  (KR) .......................... 10-2014-0032420

(51) Int. Cl.
*A61F 9/02* (2006.01)
*G02C 11/08* (2006.01)

(52) U.S. Cl.
CPC ................ *A61F 9/028* (2013.01); *G02C 11/08* (2013.01)

(58) Field of Classification Search
CPC .................................... A61F 9/028; A61F 9/02

USPC ............................................................ 2/436
See application file for complete search history.

(56) References Cited

U.S. PATENT DOCUMENTS

| | | | |
|---|---|---|---|
| 5,966,746 A * | 10/1999 | Reedy et al. | 2/436 |
| 6,601,240 B2 * | 8/2003 | Tsubooka | 2/436 |
| 6,611,966 B1 * | 9/2003 | Yamamoto et al. | 2/436 |
| 6,637,038 B1 * | 10/2003 | Hussey | 2/436 |
| 7,320,261 B1 * | 1/2008 | Hockaday et al. | 73/865.9 |
| 2003/0110552 A1 * | 6/2003 | Youmans et al. | 2/426 |
| 2004/0103469 A1 * | 6/2004 | Hussey | 2/436 |
| 2006/0119948 A1 * | 6/2006 | Matsumoto et al. | 359/624 |
| 2007/0169252 A1 * | 7/2007 | Rayl et al. | 2/435 |
| 2008/0055538 A1 * | 3/2008 | Kobayashi et al. | 351/62 |
| 2009/0077722 A1 * | 3/2009 | Welchel et al. | 2/436 |
| 2009/0100577 A1 * | 4/2009 | Kobayashi et al. | 2/436 |
| 2013/0128217 A1 * | 5/2013 | Salmini | 351/62 |
| 2013/0208229 A1 * | 8/2013 | Polegato Moretti | 351/62 |

* cited by examiner

*Primary Examiner* — Anne Kozak
(74) *Attorney, Agent, or Firm* — Cantor Colburn LLP

(57) ABSTRACT

Provided are ski goggles having a pressure balancer. At least one gasket support body, acting as a pressure balancer, is fitted in a gap maintenance gasket bonded to an outer lens plate and an inner lens plate therebetween, a vent hole is formed through the gasket support body, and a waterproof filter is attached to the vent hole. The gap maintenance gasket is divided into an upper gasket and a lower gasket. The gasket support body is disposed between the upper and lower gasket.

5 Claims, 15 Drawing Sheets

A-A' Cross section

B-B' Cross section

C-C' Cross section

SKI GOGGLES HAVING PRESSURE BALANCER

BACKGROUND OF THE INVENTION

1. Field of the Invention

The present invention relates to ski goggles having a pressure balancer (Air Cubic Equalizer), and more particularly to ski goggles of a double lens structure which has a gap maintenance gasket interposed between double lens plates, gasket support bodies acting as a pressure balancer, having a vent hole and fitted in the gap maintenance gasket, and a waterproof filter attached to the vent hole, thereby preventing goggle lenses from being deformed or dented even when external air pressure is changed as a goggle wearer goes down a slope or the like.

2. Description of the Related Art

Since ski goggles are generally used in cold weather, a goggle lens is likely to fog up due to body temperature or perspiration of a skier during use, which possibly causes an accident because of an obscured field of view.

To prevent the goggle lens from fogging, it has been practice to subject the lens to a chemical antifogging surface treatment. Such treatment produces an appreciable antifogging effect when the goggle lens has a surface temperature of about 0° C. or higher, but is not fully effective in an environment in which the surface temperature drops below 0° C. since water drops produced on the inner surface of the goggle lens are frozen.

Another method for preventing the goggle lens from fogging is to make use of a compound lens via a double lens (i.e., outer and inner lens plates) structure and form a heat insulating layer between the inner lens plate and the outer lens plate. In the case of this construction, the lens will not be fogged immediately by virtue of the heat insulating layer even when the lens has a surface temperature of about 0° C. or lower, and also remains free from fog in an environment in which the outer lens plate has a surface temperature of about 0° C. or lower. However, today's skiing or the like requires a very large quantity of physical effort and thus intensely increases a skier's body temperature and enhances a skier's sweating, which demands a more powerful antifogging effect of the goggles.

To this end, in the case of a double lens (i.e., outer and inner lens plates) structure, a gasket for sealing is interposed between the inner lens plate and the outer lens plate. However, when the ski goggles are used at a high altitude, the ski goggles are subjected to contraction and expansion due to a difference in air pressure, resulting in structural problems of the ski goggles and inconvenience in use.

In order to solve the problems of the ski goggles due to a difference in air pressure, the gasket is provided with a nonwoven or GORE-TEX® brand fabric.

However, the gasket structure with a nonwoven or GORE-TEX® brand fabric has a drawback in that it is hard to secure a uniform thickness of the lens, that is, a gap between one side portion of the inner lens plate and one side portion of the outer lens plate may be relatively large and a gap between an opposite side portion of the inner lens plate and an opposite side portion of the outer lens plate may be relatively small, thereby causing an imbalance of a gap between the inner lens plate and the outer lens plate. Especially, in the case in which air pressure is abruptly changed, since an air passage cannot be secured, contraction and expansion of the lens occur intensively. In other words, the conventional ski goggles cannot cope with a sudden change in air pressure.

In addition, when manufacturing a gasket for sealing of the double lens structure (i.e., sealing between the inner lens plate and the outer lens plate) by a press process, as shown in FIG. 15, in order to get a loop-shaped gasket, the inner section surrounded by the loop-shaped section of the gasket is taken away. Therefore, loss of a raw material is increased, and productivity is deteriorated.

SUMMARY OF THE INVENTION

Therefore, it is an object of the present invention to provide ski goggles having a pressure balancer which have a double lens structure and can prevent lenses from being deformed or dented due to a difference between internal and external air pressures of the lenses.

It is another object of the present invention to provide ski goggles having a pressure balancer which can cope with a sudden change in air pressure by securing an air passage, thereby preventing contraction and expansion of the lenses.

It is a further object of the present invention to provide ski goggles having a pressure balancer which can always maintain a constant gap between an outer lens plate and an inner lens plate and can reduce manufacturing costs by manufacturing a gap maintenance gasket divided into two or more pieces.

In accordance with an aspect of the present invention, the above and other objects can be accomplished by the provision of ski goggles having an outer lens plate, an inner lens plate and a gap maintenance gasket interposed between the outer lens plate and the inner lens plate to connect the outer lens plate and the inner lens plate, the ski goggles comprising a pressure balancer which includes at least one gasket support body fitted in the gap maintenance gasket, a vent hole formed through the gasket support body, and a waterproof filter attached to the vent hole.

The at least one gasket support body may be divided into two pieces, the vent hole may be formed through two pieces of the gasket support body, and the waterproof filter may be inserted between two pieces of the gasket support body.

The gap maintenance gasket may be divided into two or more pieces, and the gasket support body may be removably fitted between the divided pieces of the gap maintenance gasket.

The gasket support body may be made of any one selected from synthetic resin, metal, rubber and ceramic.

The waterproof filter may allow external air to flow in a space between the outer lens plate and the inner lens plate through the vent hole so that internal and external pressures of the outer lens plate and the inner lens plate can be balanced, but may prevent moisture from entering the space between the outer lens plate and the inner lens plate.

The waterproof filter may be formed as a sticker type which has an adhesive agent on one surface thereof so as to be attached and detached.

The waterproof filter may be made of a tetrafluoroethylene resin fiber layer.

The pressure balancer may further include a moisture removing cartridge which is removably inserted into the vent hole.

As is apparent from the above description, at least one gasket support body, acting as a pressure balancer, is fitted in the gap maintenance gasket bonded to the outer lens plate and the inner lens plate therebetween, the vent hole is formed through the gasket support body, and the waterproof filter is attached to the vent hole. Accordingly, even when external air pressure is changed, the lenses can be prevented from being deformed or dented. Further, even if the surface temperature of the lens drops below 0° C., water drops produced on the inner surface of the lens are hardly frozen, and antifogging effect can be enhanced.

In addition, the goggles according to the present invention can solve the problem of increase in manufacturing costs due to waste of a raw material for manufacturing the gap maintenance gasket because a conventional loop-shaped gasket is cut as a whole out of Ethylene Vinyl Acetate (EVA) foam and double-sided adhesive tape and an inner section surrounded by a loop-shaped section of the gasket is taken away. Therefore, the present invention is very useful in the ski goggles industry.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
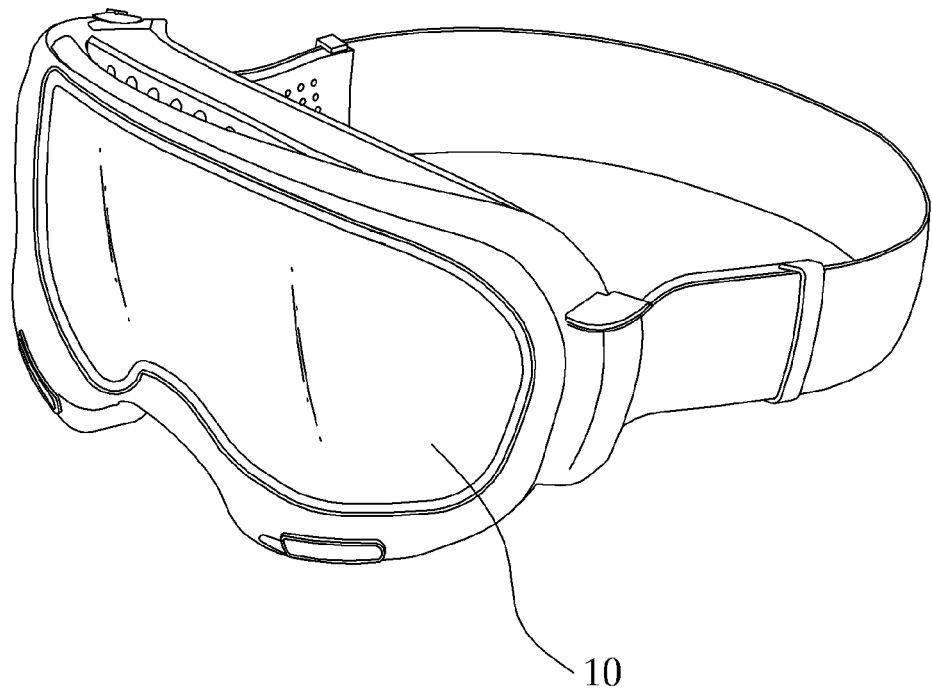
FIG. 1 is a perspective view illustrating conventional ski goggles.

Now, ski goggles having a pressure balancer according to preferred embodiments of the present invention will be described in detail with reference to the annexed drawings.

It should be understood that the terms used in the specification and appended claims should not be construed as limited to general and dictionary meanings but be construed based on the meanings and concepts according to the spirit of the present invention on the basis of the principle that the inventor is permitted to define appropriate terms for the best explanation.

The preferred embodiments described in the specification and shown in the drawings are illustrative only and are not intended to represent all aspects of the invention, such that various equivalents and modifications can be made without departing from the spirit of the invention.

According to the present invention, at least one gasket support body, acting as a pressure balancer, is fitted in a gap maintenance gasket interposed between an outer lens plate and an inner lens plate, a vent hole is formed through the gasket support body, and a waterproof filter is attached to the vent hole. Accordingly, a gap between the outer lens plate and the inner lens plate is maintained constant, internal and external pressures of the lens plates are balanced, and moisture permeation is prevented.

To achieve the foregoing effects, ski goggles according to an exemplary embodiment of the present invention comprise an outer lens plate 10, an inner lens plate 20 and a gap maintenance gasket interposed between the outer lens plate 10 and the inner lens plate 20 to connect them. Gasket support bodies 40 and 40', acting as a pressure balancer, are respectively fitted in both side portions of the gap maintenance gasket, a vent hole 42 is formed through each of the gasket support bodies so that external air can be introduced into an internal space 60 between the outer lens plate 10 and the inner lens plate 20, and a waterproof filter 50 is attached to an outer surface of the vent hole 42 to prevent moisture from permeating through the vent hole 42.

Alternatively, ski goggles according to another exemplary embodiment of the present invention comprise an outer lens plate 10, an inner lens plate 20 and a gap maintenance gasket interposed between the outer lens plate 10 and the inner lens plate 20 to connect them. Gasket support bodies, acting as a pressure balancer, are respectively fitted in both side portions of the gap maintenance gasket, vent holes 42-1 and 42-1' are formed through the gasket support bodies 40-1 and 40-1' so that external air can be introduced into an internal space 60 between the outer lens plate 10 and the inner lens plate 20, and a waterproof filter 50 is inserted between the vent holes 42-1 and 42-1' in order to prevent moisture from permeating through the vent holes 42-1 and 42-1'.

The gasket support bodies are made of any one selected from synthetic resin, metal, rubber and ceramic. Both sides of the gasket support bodies may be provided with double-sided adhesive tape adhering thereto or may be coated with an adhesive agent.

The waterproof filter is made of a tetrafluoroethylene resin fiber layer.

Figure 2:
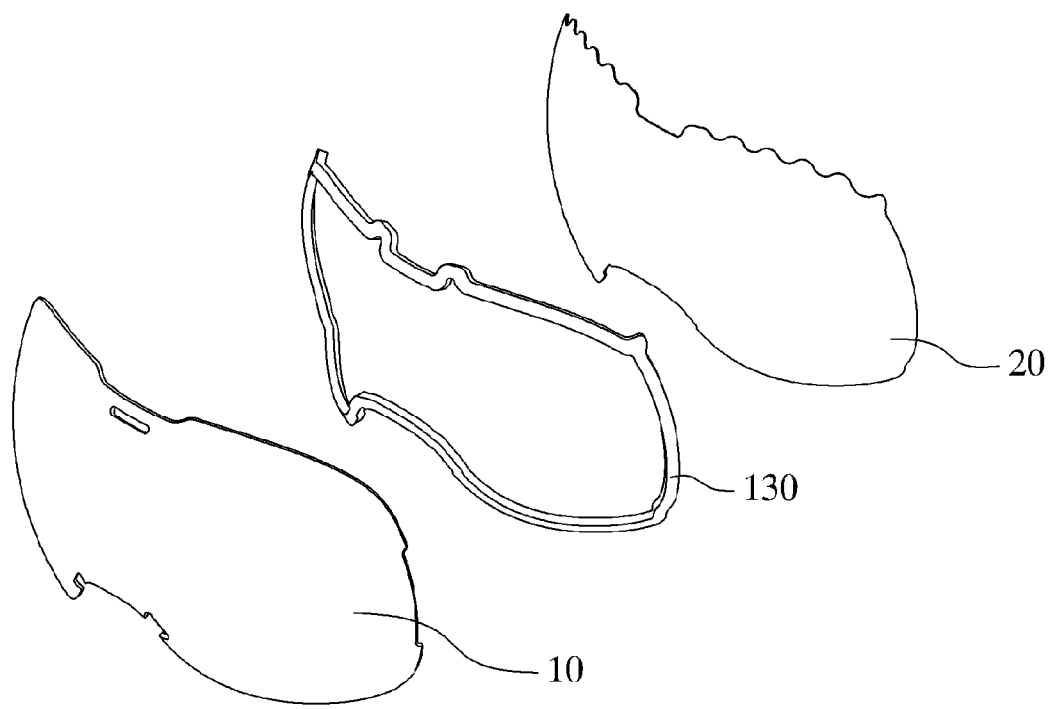
FIG. 2 is an exploded perspective view of conventional ski goggles.
Figure 3:
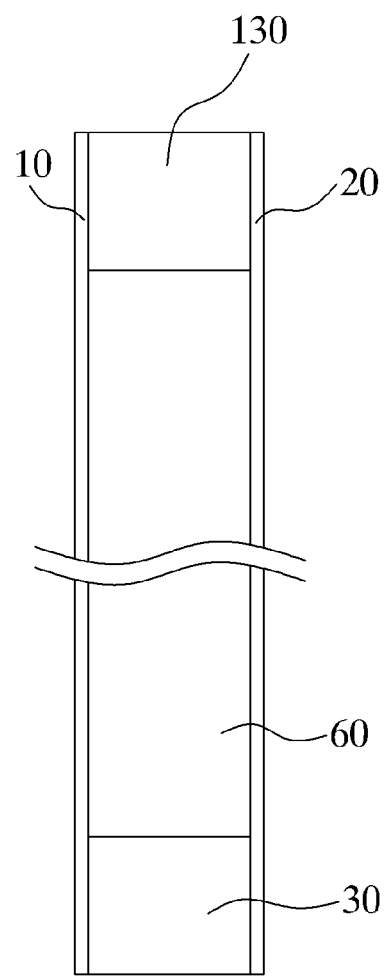
FIG. 3 is a cross-sectional view of conventional ski goggles.

As shown in FIGS. 1 through 3, conventional goggles comprise an outer lens plate 10, an inner lens plate 20 and a gap maintenance gasket 130 interposed between the outer lens plate 10 and the inner lens plate 20 to connect them.

As shown in FIGS. 4 through 14, a gap maintenance gasket 30 used in goggles according to exemplary embodiments of the present invention is made of synthetic resin foam or rubber. The gap maintenance gasket 30 used to connect the outer lens plate 10 and the inner lens plate 20 in the goggles according to the present invention, as shown in FIGS. 4 through 14, may be replaced by a rim which has a different shape and is made by injection molding of a hard material.

Figure 4:
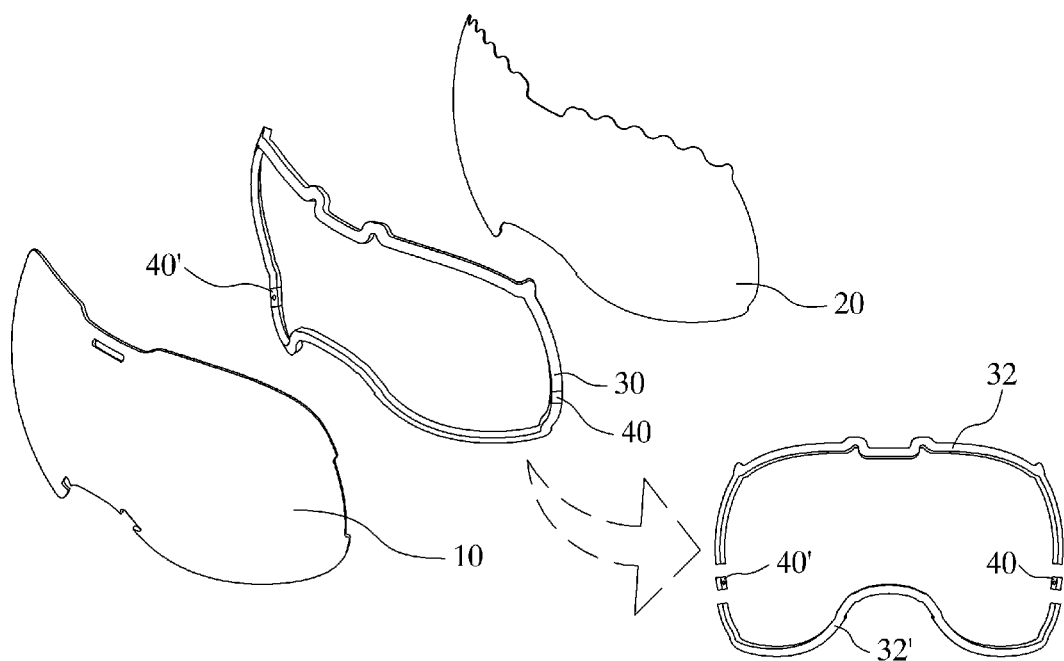
FIG. 4 is a perspective view illustrating ski goggles having a pressure balancer according to an exemplary embodiment of the present invention.
Figure 5:
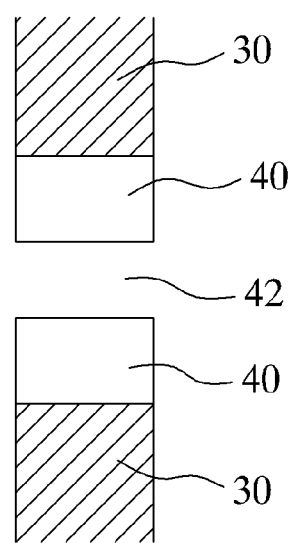
FIG. 5 is a cross-sectional view of a gap maintenance gasket used in ski goggles according to an exemplary embodiment of the present invention.
Figure 6:
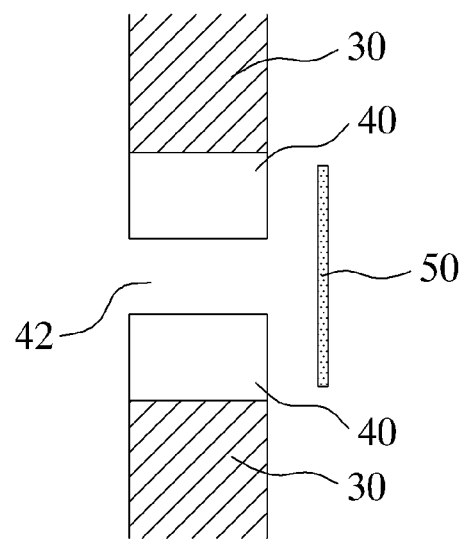
FIG. 6 is a cross-sectional view of a gap maintenance gasket used in ski goggles according to an exemplary embodiment of the present invention.
Figure 7:
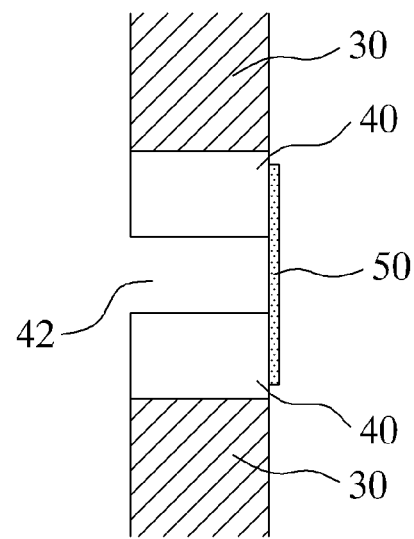
FIG. 7 is a cross-sectional view of a gap maintenance gasket used in ski goggles according to an exemplary embodiment of the present invention.
Figure 8:
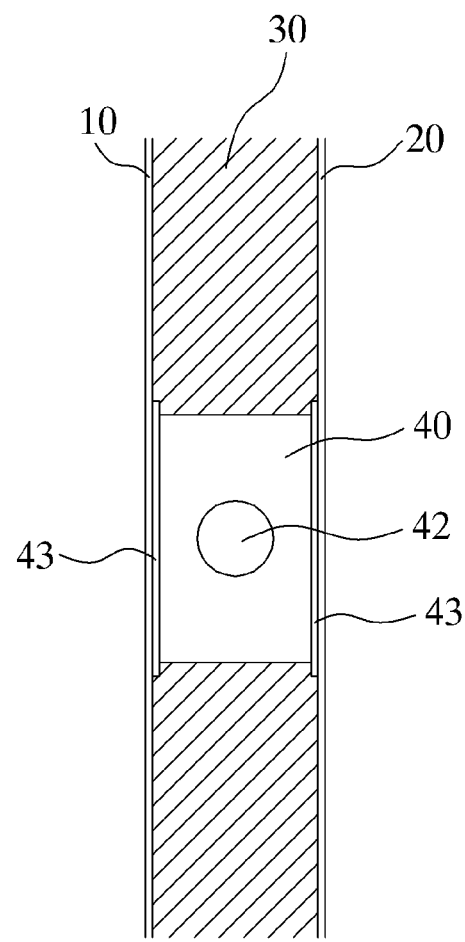
FIG. 8 is a cross-sectional view of a gap maintenance gasket used in ski goggles according to an exemplary embodiment of the present invention.
Figure 9:
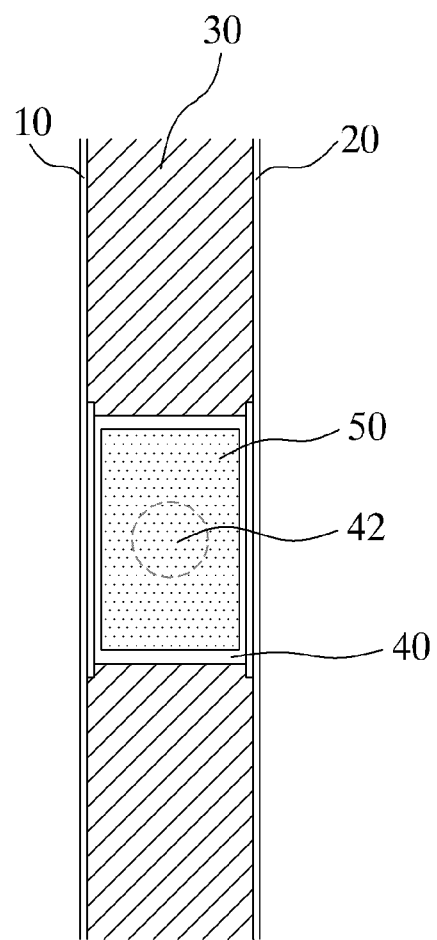
FIG. 9 is a cross-sectional view of a gap maintenance gasket used in ski goggles according to an exemplary embodiment of the present invention.
Figure 10:
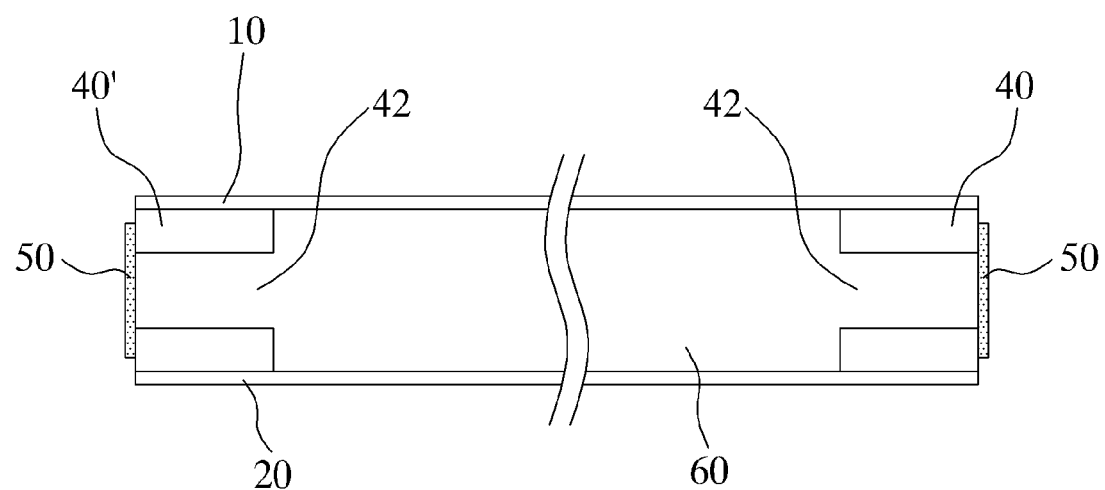
FIG. 10 is a cross-sectional view of ski goggles according to an exemplary embodiment of the present invention.
Figure 11:
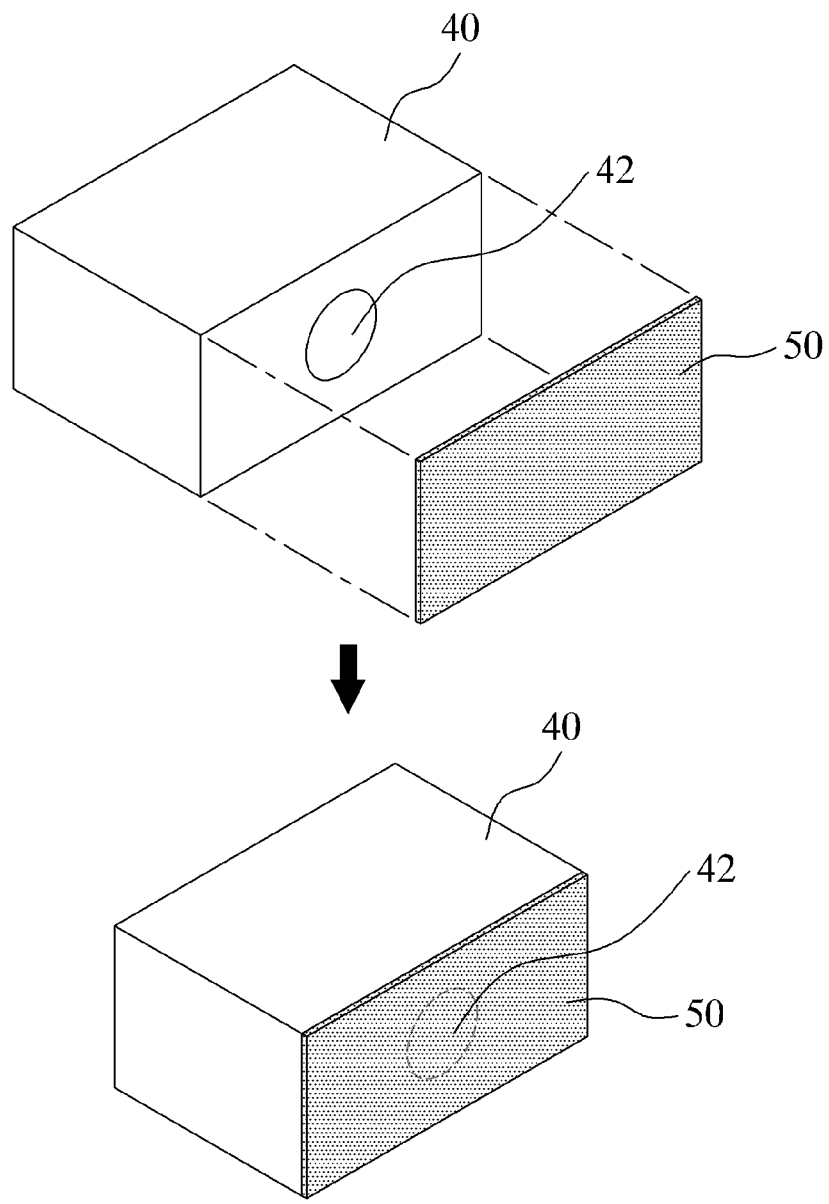
FIG. 11 is an exploded perspective view of a gasket support body used in ski goggles according to an exemplary embodiment of the present invention.
Figure 12:
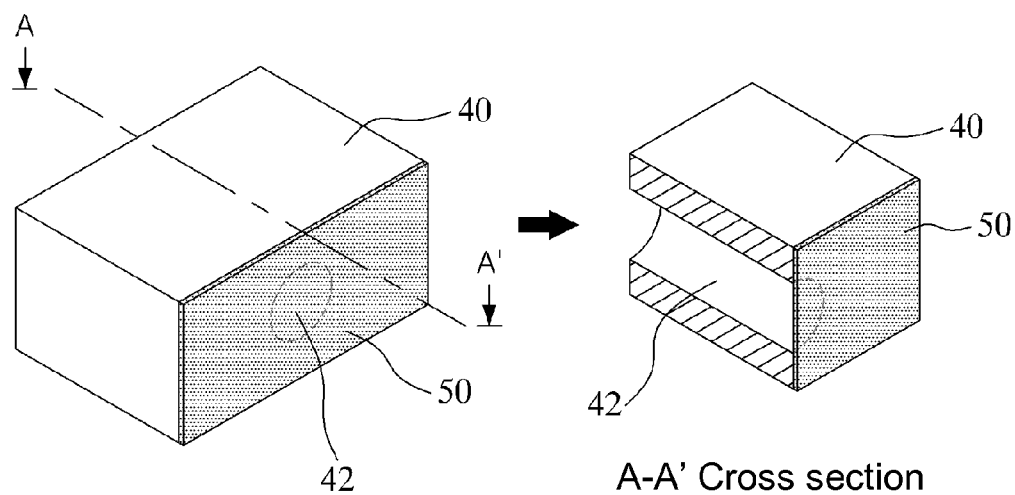
FIG. 12 is an exploded perspective view of a gasket support body used in ski goggles according to an exemplary embodiment of the present invention.
Figure 13:
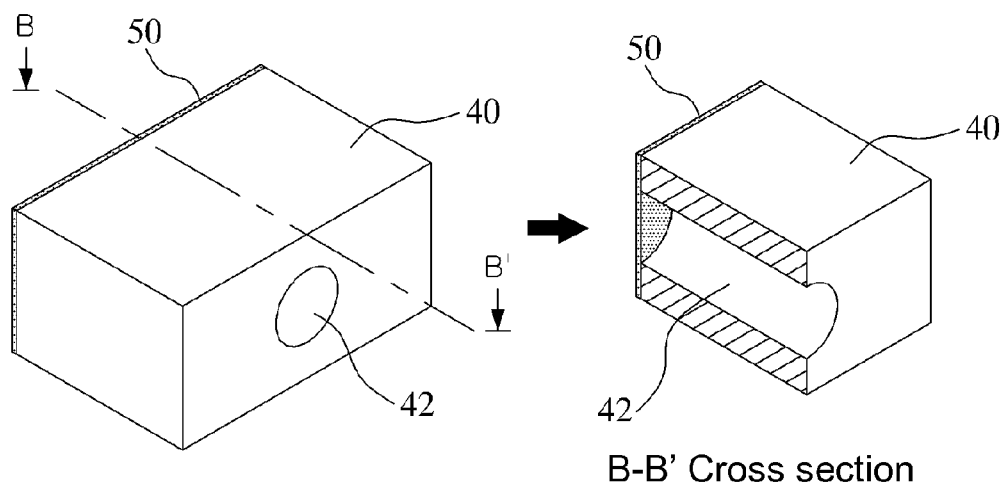
FIG. 13 is an exploded perspective view of a gasket support body used in ski goggles according to an exemplary embodiment of the present invention.

As shown in FIG. 4, the goggles according to the present invention further include gasket support bodies 40 and 40' which are respectively fitted in both side portions of the gap maintenance gasket 30. The gasket support bodies 40 and 40' function as a pressure balancer. Although external air pressure is changed as a goggle wearer goes down a slope or the like, the gasket support bodies 40 and 40' can prevent the lens plates 10 and 20 from being deformed or dented.

In detail, as shown in FIG. 4, the gap maintenance gasket 30 is divided into an upper gasket 32 and a lower gasket 32', and the gasket support bodies 40 and 40', acting as a pressure balancer, are respectively fitted between the upper gasket 32 and the lower gasket 32' so as to prevent the lens plates 10 and 20 from being deformed or dented even when external air pressure is changed as a goggle wearer goes down a slope or the like.

As shown in FIGS. 4 through 13, a vent hole 42 is formed through the gasket support body 40 which is a pressure balancer so that external air can be introduced into an internal space 60 between the outer lens plate 10 and the inner lens plate 20. Since external air can be introduced into the internal space 60 between the outer lens plate 10 and the inner lens plate 20 through the vent hole 42, the lens plates 10 and 20 are prevented from being deformed or dented due to a difference in air pressure between the internal space 60 and the external atmosphere.

In addition, as shown in FIGS. 4 through 13, a waterproof filter 50 is attached to the outer surface of the vent hole 42 of the gasket support body 40 which is a pressure balancer in order to prevent moisture from permeating through the vent hole 42. Accordingly, even when external air pressure is changed as a goggle wearer goes down a slope or the like, the lens plates 10 and 20 are prevented from being deformed or dented.

Figure 14:
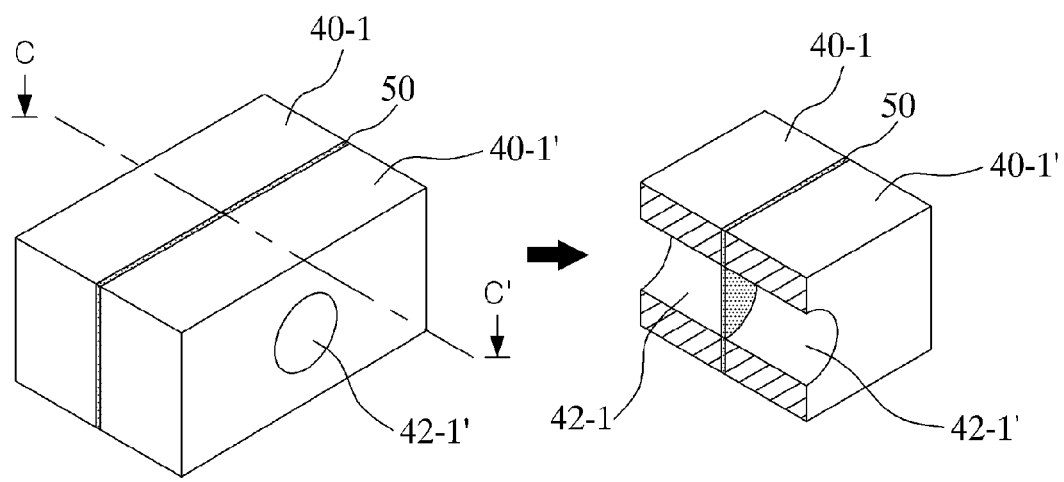
FIG. 14 is an exploded perspective view of a gasket support body used in ski goggles according to an exemplary embodiment of the present invention.

As shown in FIG. 14, gasket support bodies 40-1 and 40-1' according to another exemplary embodiment of the present invention are respectively formed with vent holes 42-1 and 42-1'. A waterproof filter 50 is inserted between the vent hole 42-1 of the gasket support body 40-1 and the vent hole 42-1' of the gasket support body 40-1' in order to prevent moisture from permeating through the vent holes 42-1 and 42-1'.

The gap maintenance gasket 30 is interposed between an edge portion around the outer lens plate 10 and an edge portion around the inner lens plate 20 which oppose each other. The gap maintenance gasket 30 and the lens plates 10 and 20 are adhered to each other by double-sided adhesive tape.

A gap between the outer lens plate 10 and the inner lens plate 20 is preferably set to be about 2 mm. Preferably, the internal space 60 between the outer lens plate 10 and the inner lens plate 20 functions as a heat insulating layer. A thickness of each of the lens plates 10 and 20 is preferably set to be about 0.6 mm.

The gap maintenance gasket 30 is preferably made of a soft material, such as elastic synthetic resin, rubber or the like.

As described above, the vent hole 42 formed through the gasket support body 40 allows external air to flow into the internal space 60 between the outer lens plate 10 and the inner lens plate 20, thereby preventing the lens plates 10 and 20 from being deformed or dented even when external air pressure is changed as a goggle wearer goes down a slope or the like.

The waterproof filter 50 functions to block moisture permeation. As the water filter 50, a water-repellant vent sheet which prevents external moisture from entering the internal space 60 which is a heat insulating layer between the outer lens plate 10 and the inner lens plate 20 while permitting air to pass therethrough is employed.

This waterproof filter 50 is made of a sheet of air-permeable base material such as nylon cloth to which a continuous porous material such as a tetrafluoroethylene resin fiber layer is bonded. The tetrafluoroethylene resin fiber layer has a drawn, very tough, ductile and fine fiber structure. The layer also has many continuous pores and high water-repellency.

The waterproof filter 50 is formed as a sticker type which has an adhesive agent on one surface thereof so as to be easily attached and detached, thereby facilitating replacement. Even when external air pressure is changed as a goggle wearer goes down a slope or the like, the water-repellent vent sheet as a moisture blocking means functions to allow the internal and external pressures of the lens plates 10 and 20 to be balanced. Thus, the outer and inner lens plates 10 and 20 have no deformations and distortion of the field of vision can be prevented.

Further, when external air pressure increases, external air flows in the vent hole 42 through the waterproof filter 50. However, the waterproof filter 50 prevents moisture from entering the internal space between the outer and inner lens plates 10 and 20 even if the external air contains a large quantity of moisture or even if snow or moisture adheres to the outer surface of the waterproof filter 50. Therefore, despite the vent hole 42 for balancing pressure, fogging up of the inside of the goggle lens can be prevented.

Figure 15:
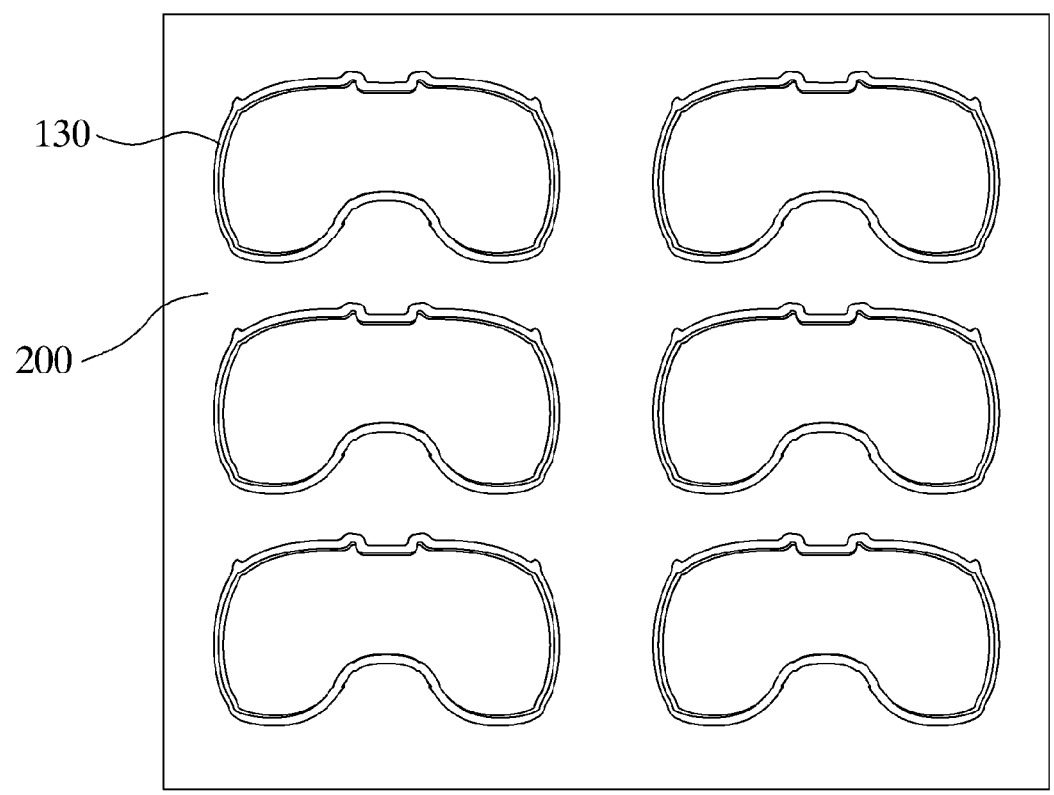
FIG. 15 is a view illustrating a state in which a gap maintenance gasket used in conventional ski goggles is cut out of a raw material.
Figure 16:
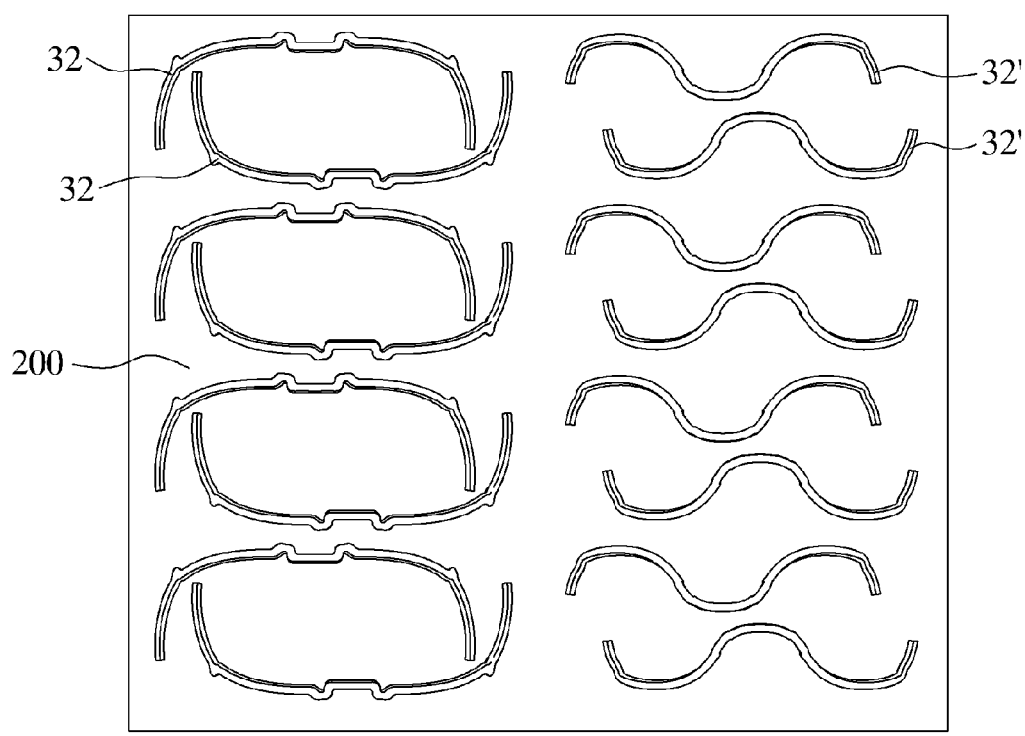
FIG. 16 is a view illustrating a state in which a gap maintenance gasket used in ski goggles according to the present invention is cut out of a raw material.
Figure 17:
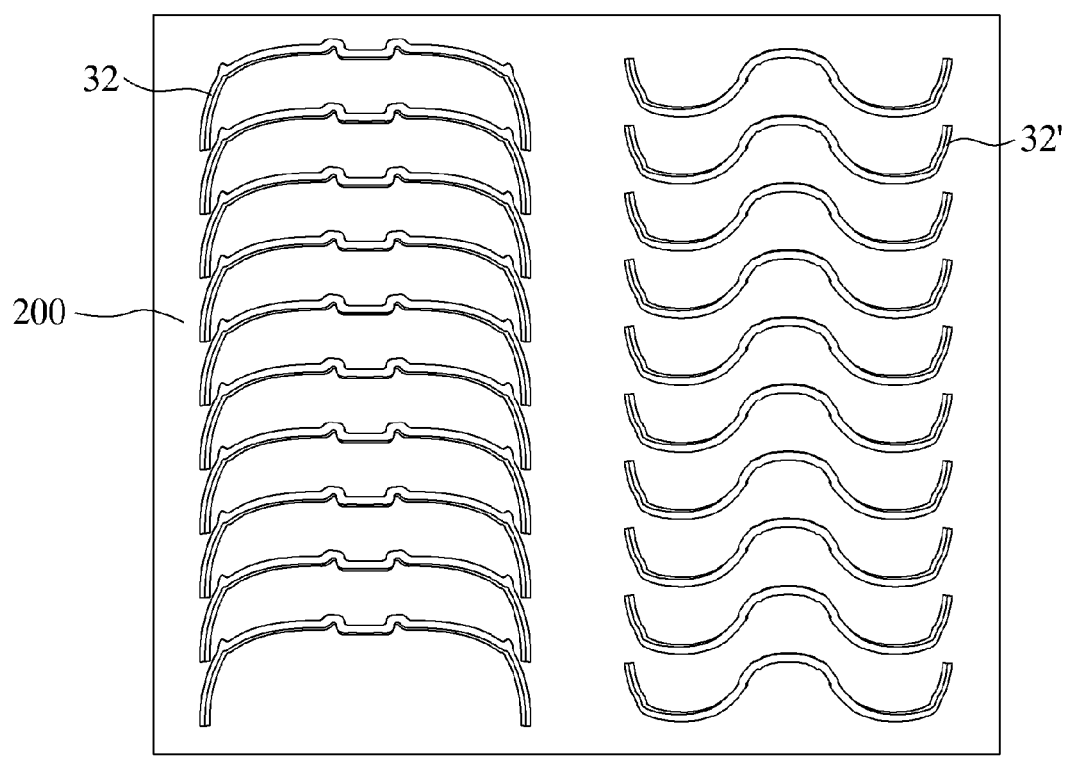
FIG. 17 is a view illustrating a state in which a gap maintenance gasket used in ski goggles according to the present invention is cut out of a raw material.

According to the embodiments of the present invention, the upper gasket 32 and the lower gasket 32' are separately manufactured by being cut out of a raw material. For example, as shown in FIGS. 16 and 17, the upper and lower gaskets 32 and 32' to be manufactured may be designed in various arrangement patterns on a raw material 200 before being cut out of the raw material 200, by which the raw material 200 for manufacturing the upper and lower gaskets 32 and 32' can be more efficiently used than when cutting the conventional loop-shaped gasket 130 as a whole out of the raw material 200 as shown in FIG. 15. The gap maintenance gasket may be divided into two or more pieces and may be bonded to the outer and inner lens plates.

A large quantity of the raw material 200 may be wasted when cutting the conventional loop-shaped gasket 130 as a whole out of the raw material 200. However, by dividing the gap maintenance gasket 30 used in the goggles according to the present invention into two or more pieces, the raw material 200 can be almost used up without waste. Accordingly, manufacturing costs of the gap maintenance gasket can be reduced and manufacturing processes can be facilitated, resulting in enhancement of productivity.

Figure 18:
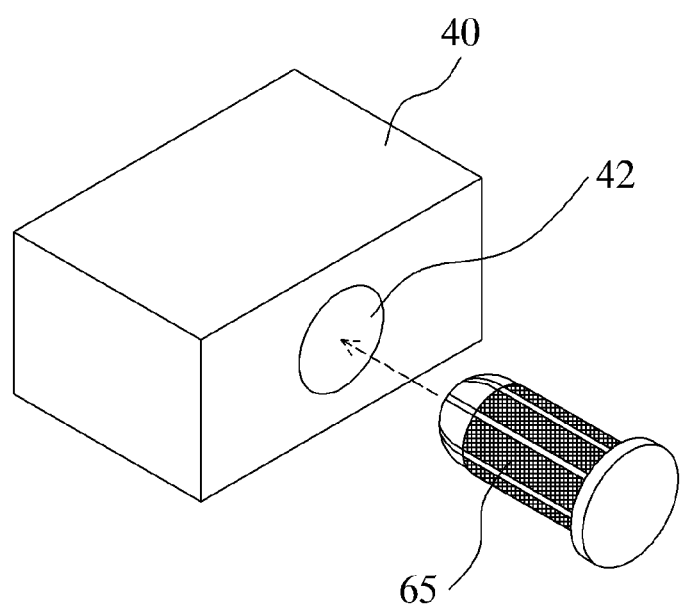
FIG. 18 is an exploded perspective view illustrating a state in which a desiccant cartridge is mounted to remove moisture from a double lens structure of ski goggles according to another exemplary embodiment of the present invention.

As shown in FIG. 18, in order to remove moisture from the double lens structure in which the outer lens plate 10 and the inner lens plate 20 are connected to each other by the gap maintenance gasket interposed therebetween, a moisture removing cartridge 65 may be additionally inserted into the vent hole 42 of the gasket support body 40.

Instead of the moisture removing cartridge 65, a desiccant cartridge may be inserted into the vent hole 42 of the gasket support body 40 in order to remove moisture.

Preferably, the moisture removing cartridge 65 is removably inserted into the vent hole 42 of the gasket support body 40. When a predetermined time has elapsed after insertion of the moisture removing cartridge 65, the moisture removing cartridge 65 is removed from the vent hole 42, and then the waterproof filter sticker is attached to the vent hole 42.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. Ski goggles comprising:
    an outer lens plate and an inner lens plate;
    a gap maintenance gasket interposed between an edge portion of the outer lens plate and an edge portion of the inner lens plate to connect the outer lens plate and the inner lens plate and define an internal space in-between, wherein the gap maintenance gasket is composed of two separate gaskets including an upper gasket and a lower gasket;
    two gasket support bodies disposed between the upper gasket and the lower gasket and connecting the upper and lower gaskets to form the gap maintenance gasket;
    a vent hole formed in each of the gasket support bodies, the vent hole being a through-hole formed from the internal space to outside; and
    a waterproof filter disposed in the vent hole; further comprising a moisture removing cartridge which is removably inserted into the vent hole.

2. The ski goggles according to claim 1, wherein the gasket support body is made of any one selected from the group consisting of synthetic resin, metal, rubber and ceramic.

3. The ski goggles according to claim 1, wherein the waterproof filter allows external air to flow in the internal space through the vent hole so that internal and external pressures of the internal space can be balanced, but prevents moisture from entering the internal space.

4. The ski goggles according to claim 3, wherein the waterproof filter is formed as a sticker type which has an adhesive agent on one surface thereof so as to be attached and detached.

5. The ski goggles according to claim 3, wherein the waterproof filter is made of a tetrafluoroethylene resin fiber layer.

\* \* \* \* \*